United States Patent [19]

Dukes et al.

[11] Patent Number: 4,990,784
[45] Date of Patent: Feb. 5, 1991

[54] NONLINEAR AVERAGING COMPENSATED MEASUREMENTS

[75] Inventors: John R. Dukes; Mason L. Thompson, both of Worthington, Ohio

[73] Assignee: Process Automation Business, Inc., Columbus, Ohio

[21] Appl. No.: 399,224

[22] Filed: Aug. 25, 1989

[51] Int. Cl.$^5$ ............................................. G01N 23/00
[52] U.S. Cl. .................................. 250/358.1; 250/559; 250/308; 356/432
[58] Field of Search ............... 250/358.1, 359.1, 360.1, 250/338.1, 341, 559, 308; 356/432, 433, 435, 444

[56] References Cited

U.S. PATENT DOCUMENTS 4,292,522 9/1981 Okumoto ........................ 250/358.1
4,301,366 11/1981 Bertin et al. ...................... 250/358.1

Primary Examiner—Janice A. Howell
Assistant Examiner—Richard Hanig
Attorney, Agent, or Firm—Chilton, Alix & Van Kirk

[57] ABSTRACT

Method and apparatus for measurement and control of an industrial process by detecting the average transmittance of a radiation beam which passes through the process material. A radiation source (28) having an intensity $I_o$ is positioned on one side of the material to be measured and a suitable radiation detector (32) is positioned on the other side. The transmitted radiation intensity, I, is measured by the sensor. An index Z commensurate with the degree of nonuniformity of the variable in the material is determined, and a process signal is generated from a quantitative relationship among I, $I_o$, and the index Z. In a first embodiment implementedd in a system for measurement and control of the basis weight of paper in a paper production process, the index Z is indicative of the nonuniformity of the material mass distribution in the sheet and is determined by measurements with a separate formation gauge operating on-line with, but independently of, the basis weight sensor. In a second embodiment of the invention implemented in such a paper making process, the index Z commensurate with the degree of nonuniformity for the mass in the material, is derived from the standard deviation of the detected radiation intensity signal, or the equivalent standard deviation of the basis weight output signal.

20 Claims, 5 Drawing Sheets

NONLINEAR AVERAGING COMPENSATED MEASUREMENTS

BACKGROUND OF THE INVENTION

The present invention relates to the measurement of industrial processes, and more particularly, to measurement and control systems and methods of measurement which rely on detecting variations in a beam of energy which is altered by transmittance, scattering, or fluorescence interactions with the process material being measured. An example is a measuring system which utilizes nuclear radiation as the energy source.

Many measurement sensors have a nonlinear response with respect to the process variable being measured. When such sensors are operated in a manner such that the sensor output represents an average of the variable to be measured over some area of the measured material, instrument errors due to nonlinear averaging may result if the process material is nonhomogeneous. Specific examples include the use of beta radiation for the measurement of basis weight in the paper making industry, or the use of gamma or x-radiation to measure the weight per area of fiberglass insulation batts being produced.

Typically, the weight per unit area of sheet material, or basis weight, is measured on-line during production of the sheet by scanning the measurement sensors back and forth across the width of the sheet as the material moves along the process line. In the case of a transmission beta gauge, a beam of beta particles is emitted from a radiation source into one side of the sheet material and the transmitted radiation is detected on the other side. The transmitted radiation varies approximately exponentially as a function of the thickness or weight per unit area of the sheet. The radiation beam is usually collimated so that it passes through some finite surface area of the measured material and the transmitted radiation represents an average basis weight for that portion of the sheet. If the material has a nonuniform distribution of mass within the measurement area, then nonlinear exponential averaging will occur which is an undesirable source of measurement error.

SUMMARY OF THE INVENTION

It is an object of this invention to provide a method and apparatus to compensate process measurements for the inherent nonlinear averaging resulting from the nonuniform distribution of a given variable in the industrial process where the material is being measured with an instrument that has a nonlinear response to that variable.

The invention includes a method and apparatus for measurement and control of an industrial process by detecting the apparent average transmittance or emission of a radiation beam or the like which passes through the process material and correcting or compensating with an index commensurate with the degree of nonuniformity of the material.

In an illustrative example, a radiation source having an intensity $I_o$ is positioned on one side of the material to be measured and a suitable radiation detector is positioned on the other side. The transmitted radiation intensity, I, is less than the incident intensity, $I_o$, and is the summation of the contributions from all of the individual radiation particles or photons which reach the detector. In a nonuniformly distributed material, the individual transmitted radiations interact nonlinearly so that the summation is influenced by the degree of material nonuniformity. An index Z commensurate with the degree of nonuniformity of the variable in the material is then determined, and a process signal is generated from a quantitative relationship among I, $I_o$, and the index Z.

In one embodiment, the step of determining the index Z includes measuring the nonuniformity of the variable independently of the steps or apparatus associated with the source beam $I_o$ and the detected beam I.

In another embodiment, the step of determining the index Z includes measuring or estimating the average transmitted intensity, $I_{avg}$, over a short period of time due to a plurality of instantaneous measurements and determining a statistical relationship between the instantaneous measurements and the average measurement.

When the first embodiment is implemented in a system for measurement and control of the basis weight of paper in a paper production process, the index Z is indicative of the nonuniformity of the material mass distribution in the sheet and is determined by measurements with a separate formation gauge operating on-line with, but independently of, the basis weight sensor.

When the second embodiment of the invention is implemented in such a paper making process, the index Z commensurate with the degree of nonuniformity for the mass in the material, is derived from the standard deviation of the detected radiation intensity signal, or the equivalent standard deviation of the basis weight output signal.

These embodiments can be implemented similarly for sensors where the measurements are based upon radiation scattered from the process material being measured or from fluorescence radiation produced in the process material, or where tracers are incorporated into the process materials and their emitted radiations are measured to derive the thickness or weight per unit area of the material. Although the preferred embodiments of the invention are illustrated herein with examples using nuclear radiation or x-rays, the invention is applicable to many other forms and types of energy for which the interactions of that energy with the variables of interest are nonlinear. This includes such radiation as visible light, infrared waves, microwaves, sonic waves, and the like.

BRIEF DESCRIPTION OF THE DRAWINGS

The preferred embodiments of the invention will be described below with reference to the accompanying drawings in which.

DESCRIPTION OF THE PREFERRED EMBODIMENT

Figure 1:
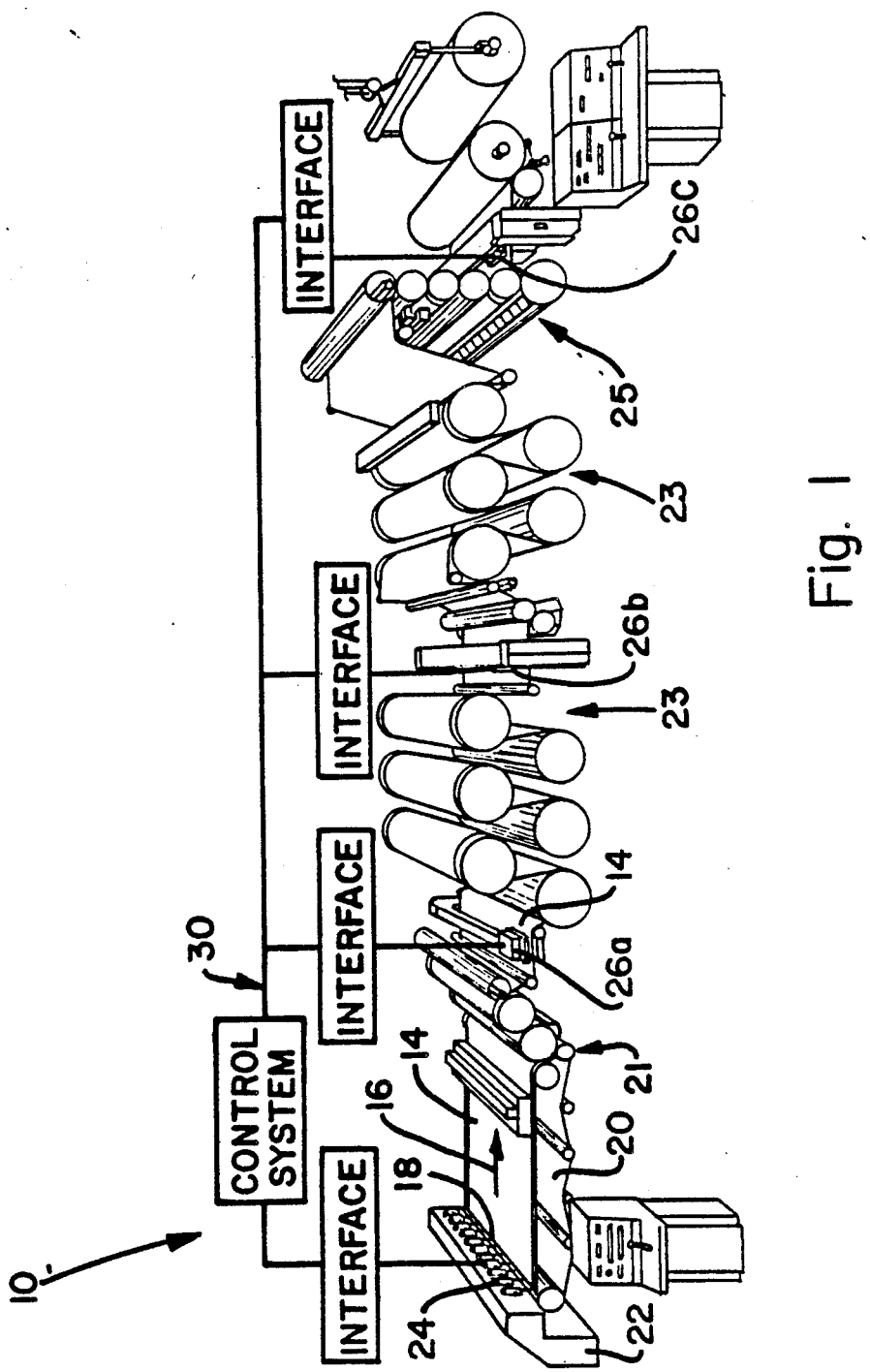
FIG. 1 is a schematic illustration of a paper making process in which the basis weight and formation gauges are used in process measurement and control.

FIG. 1 is a schematic illustration of an industrial process, and more particularly, a process 10 for the production of paper in sheet form. In the example of the invention described herein, the basis weight of the paper sheet 14 is to be measured and controlled as the paper is produced and travels in the direction indicated by arrow 16. Basis weight is the weight per unit area of the sheet which is calculated by multiplying the sheet density times its thickness. The sheet of paper 14 as produced, emerges initially as a water based slurry of fibers and chemical additives through a discharge slot 18, called the slice, in the head box 22. This slurry flows onto a moving screen 20, which is referred to as the wire, where some of the water is withdrawn by gravity and vacuum boxes so that a sheet of paper begins to form. The slice openings 18 across the width of the head box 22 are adjusted by actuators 24 to control the flow of slurry onto the wire 20 which directly affects the final basis weight of the paper sheet. From the wire 20, the paper sheet 14 continues on through press rolls 21 and high temperature dryers 23 to remove more moisture. The sheet may also go through processes that apply sizing and coatings and then remove excess water again by passing through additional dryer sections. The sheet achieves its final surface finish and thickness (caliper) by going through calendar stacks 25 before it is rolled up into reels of paper at the end of the process line.

"Beta gauge" basis weight sensors 26a, 26b and 26c may be operated at a number of locations along the paper machine in the paper making process to achieve the desired process measurements and control via signal interface and control system 30. Typically, the sensors are located after the press rolls near the exit from the wire section, in mid-machine locations after the drying ovens and before and after sizing and coatings are applied, and finally at the reel end just before the final paper product is rolled up into large reels of paper. At a given gauge location, the configuration of the material remains substantially uniform, e.g., a single, flat sheet.

Figure 2:
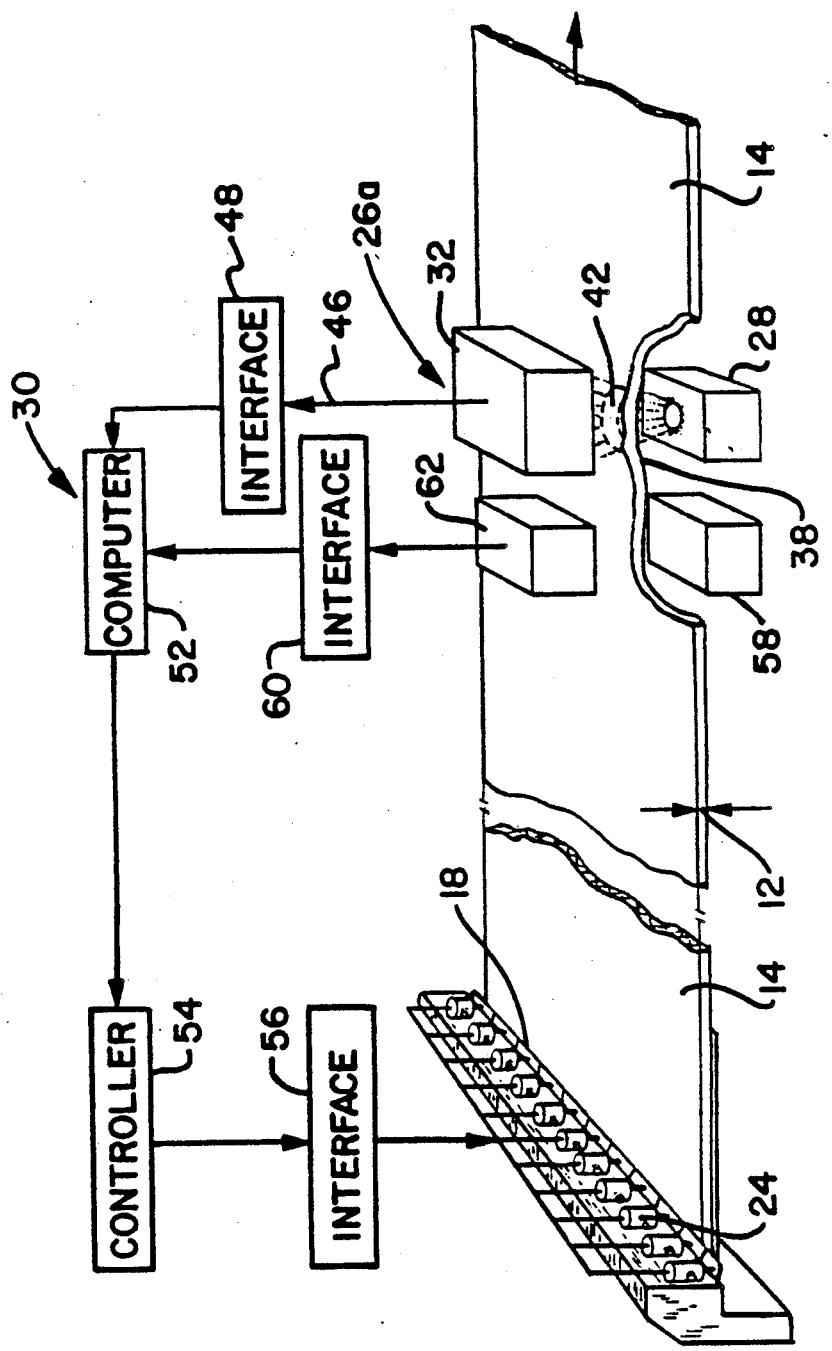
FIG. 2 is a schematic illustration of the basis weight measurement and control system in accordance with the invention.

FIG. 2 shows a simplified basis weight gauge and control system 30 in accordance with the present invention. This nucleonic basis weight sensor includes a sourcehead 28 which contains the beta emitting radioisotope, and a detector head 32 for detecting the beta particles. These heads are positioned in fixed vertical relation on either side of the paper sheet 14, downstream from the slice actuators 24. The source head 28 includes radiation beam collimation and beam shaping components to define a beam of radiation which then impinges on the lower surface 38 of sheet 14. The radiation beam interacts by one or more nuclear processes with the air column and the sheet material in the measuring gap between the heads 28, 32. A portion of the radiation beam is transmitted through the full thickness 12 of sheet material and exits through the measuring area 42, and enters the detector head 32. The circuitry associated with the detector head 32 is responsive to the total number of beta particles, and their kinetic energies, that enter the ionization chamber (not shown) in detector head 32 and produces an output signal commensurate therewith.

If the sheet material 14 were of homogeneous density, the radiation intensity I transmitted through the sheet and detected by the detector 32 would be defined by the relationship, $$I = I_o e^{-upt} = I_o e^{-uw} \quad (1)$$

where $I_o$ = radiation beam intensity detected in the absence of sheet material I = radiation beam intensity detected in the presence of sheet material u = mass attenuation coefficient (cm²/g)

p = density of the material (g/cm³)

t = thickness of the material (cm)

w = pt = basis weight (g/cm²) In equation (1), u depends upon the particular type of nuclear radiation used, its energy spectrum, energy spectrum modifications by the sensor geometry, the detector's spectral response characteristics, and the composition of the material being measured. For energy spectra which are not monoenergetic, the material being measured acts as an energy dependent filter and hence the value of u may also be a function of the thickness or basis weight of the sheet being measured. Since the final output of a gauging system will normally be expressed in basis weight units, w, equation (1) can be expressed as, $$w = -\ln(I/I_o)/u \quad (2)$$

Nuclear radiation sources typically employed with such beta gauges include Sr-90, Kr-85 and Pm-147. The radioisotope selected for a given application depends primarily upon the range of basis weight to be measured.

Although u is a complex variable, it can be modeled and if done properly, that model will remain fixed for a given nuclear source, sensor geometry, and measured process material combination. A number of models have been developed. One such model represents u by the polynomial relationship, $$u = u_o + u_1 \ln(I/I_o) + u_2 \ln^2(I/I_o) + u_3 \ln^3(I/I_o) + \ldots \quad (3)$$

The values $u_o, u_1, u_2, u_3, \ldots$, often referred to as the sensor head constants, are obtained during a calibration procedure in which Mylar samples of different basis weights are measured in the beta gauge represented by components 28, 32 in FIG. 2. Mylar is a stable homogeneous material which attenuates radiation in a manner similar to paper. The quantitative relationship between transmittance and basis weight for the Mylar samples and many types of paper, might even be represented by the same curve, having a general shape typified by FIG. 3 and dependent upon the expression (3) for u.

The control system depicted in FIG. 2 takes into account the foregoing considerations such that the detector output 46 is processed through an interface 48 and delivered to a computer 52, in which the basis weight w is continually computed as the beta gauge moves back and forth across sheet 14. These computed basis weights are compared to target values stored in the computer 52. The target values are based on the settings in controller 54, such that a control signal is passed through output interface 56 to actuators 24.

Figure 3:
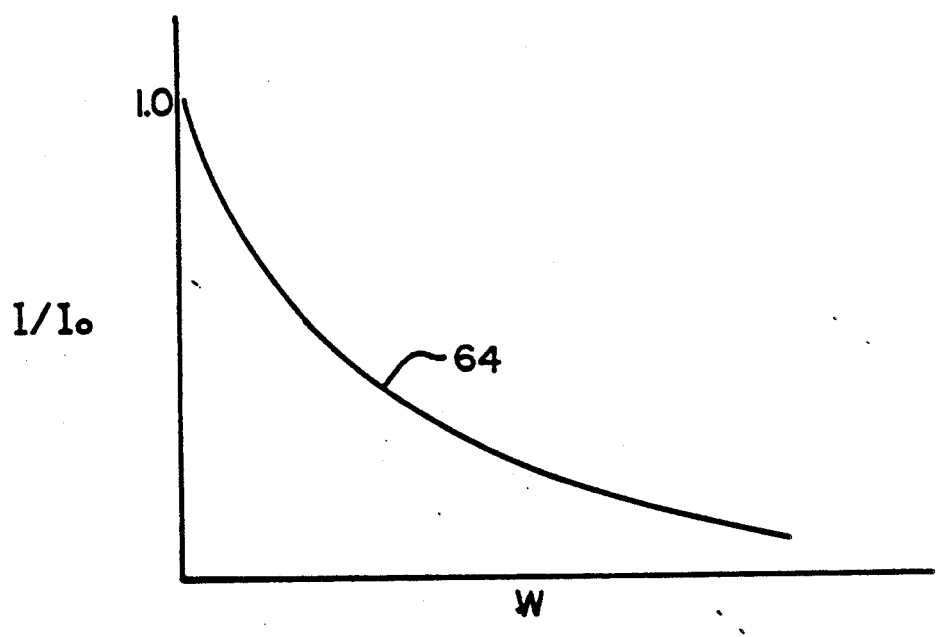
FIG. 3 is a graphic representation of the exponential relationship between the radiation beam transmittance of the basis weight gauge, and basis weight, for a uniform sheet of the homogeneous material.

FIG. 3 illustrates the exponential shape of the transmittance curve. If a sheet of material having a given basis weight were to attenuate 50% of the radiation beam (transmittance of 0.50), a sheet of material having twice that basis weight will not attenuate 100% of the radiation because of the exponential nature of the transmittance curve. The double weight sheet would actually attenuate approximately 75% of the radiation (transmittance of 0.25). This introduces a potentially serious problem when measuring nonhomogeneous materials where a high degree of nonhomogeneity exits within the small measuring area 42 of the measurement sensor. The radiation transmitted through the light weight portions of the sheet is attenuated by a greater proportion relative to its basis weight than that transmitted through the heavier portions of the sheet. This means that the average transmitted radiation intensity I, over the sensor's measuring area, does not correlate directly with the average basis weight for the same measurement area. Hence, a measurement error is introduced when the average radiation signal $I/I_o$ is converted to basis weight units w via the transmittance calibration curve 64.

This nonlinear averaging error tends to be more severe for light weight paper sheets, raw stock grades, and uncoated paper sheets because the range, or percent change, of point-to-point basis weights varies the greatest from the lowest density spots to the highest density spots within a small region of the sheet. In the limit, the lowest density spots may even be holes through which radiation passes without any attenuation. The high density spots can literally be macroscopic chunks of wood or other material making up the sheet. This is easily visualized by simply holding a single layer of tissue up to a strong light and viewing the holes and dense areas. This nonuniform mass distribution is referred to as the "formation" of the sheet. With heavier sheets the ratios of basis weights from the high density spots to the low density spots tend to be much smaller because the sheet is much thicker and there are many more layers of fibers and fillers in the path of the radiation beam.

The formation quality of paper sheets improves when coatings, such as clay, latex or titanium dioxide, are applied to the sheet because these materials fill the void spaces between the paper fibers and provide a much more uniformly distributed mass of materials. So the nonlinear averaging errors significantly diminish and tend to disappear.

In multiple gauge systems used to determine and control coating weights, the nonlinear averaging problem can be an even more significant source of measurement error than for sheet basis weight measurements. These systems have one basis weight sensor measuring the raw stock or uncoated paper just before the coating is applied and a second or even third sensor measuring the sheet after coating. The difference between the after-coating basis weight and the before-coating basis weight represents the coating weight (either wet or dry depending upon where the measurements are made). Coating weights are generally very light compared to the base sheet so the coat weight signal typically is represented by the small difference between two large signals. Any nonlinear averaging error in the before coat signal may represent a large portion of the difference signal an hence introduces a large measurement error in the coat weight.

The magnitude of the nonlinear averaging error is also a function of the radiation transmittance value. In a conventional gauge, the lower the transmittance value, i.e. the further away from a value of 1.0 as shown in FIG. 3, the greater the nonlinearity error. For example, assume a theoretical case where a nonhomogeneous sheet is comprised of only two different point-to-point basis weights, the lowest weight being 50% of the highest weight, and both weights are equally present within the sensor's measuring area, 42. In comparing the indicated basis weight readings for the nonhomogeneous material to those of homogeneous material having the same average basis weights, the calibration shifts for the nonhomogeneous materials are: 1.24% at $I/Io=0.800$; 3.82% at 0.500; and 8.54% at 0.200.

In accordance with the present invention, an index commensurate with the degree of nonuniformity of the variable being measured, i.e. mass or weight per unit area in the described embodiment, is determined and the process measurement signal is generated from a quantitative relationship including the index.

In the context of measuring the basis weight of a paper sheet, the relationship (3) may be used to define the measured process basis weight as follows:

$$w = -K \ln(I/I_o)/(u_o + u_1 \ln(I/I_o) + u_2 \ln^2(I/I_o) + u_3 \ln^3(I/I_o)) \quad (4)$$

where K is a stored constant for expressing basis weight in units of grams per square meter, or other suitable basis weight units.

Figure 4:
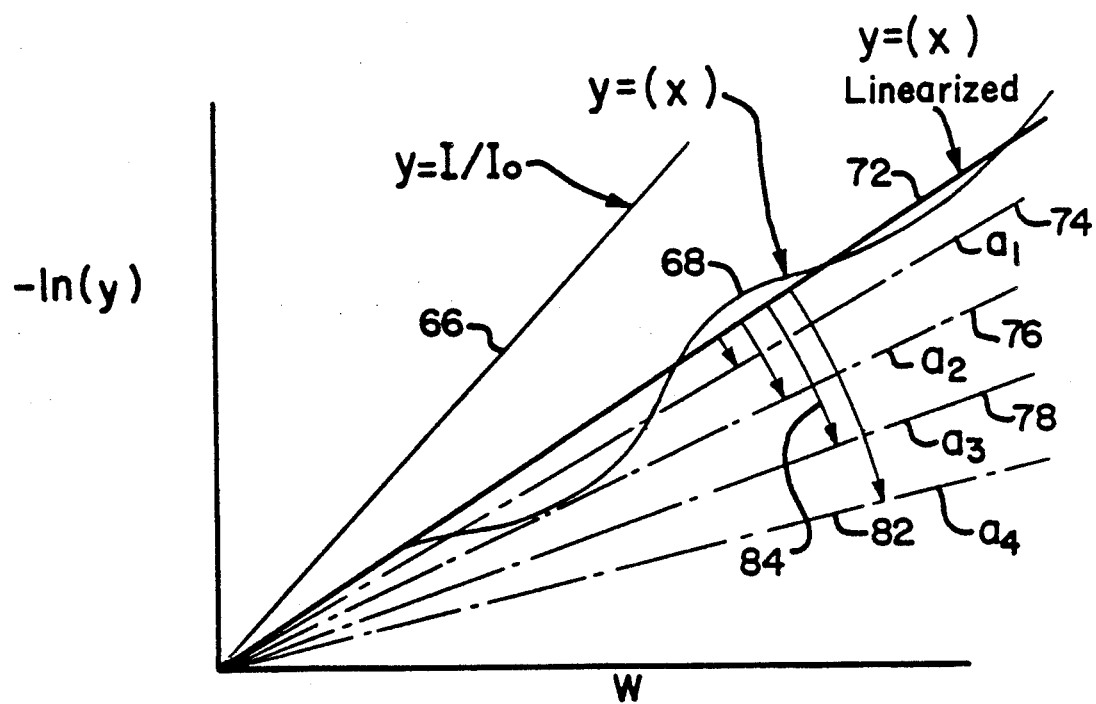
FIG. 4 is a graphic representation of how the relationship between radiation beam transmittance and basis weight is corrected for sheet mass nonuniformity in accordance with one embodiment of the invention.

If u were a constant with respect to basis weight, a plot of $-\ln(I/Io)$ as a function of basis weight, w, would provide a straight line such as that indicated by curve 66 in FIG. 4. However, for the beta gauge being described in this embodiment, u may vary with basis weight and might yield a curve such as illustrated abstractly by curve 68. Through the use of an analytical model like equation (4) where u is represented as a third order polynomial, such as in equation (3), appropriate values of the coefficients can be determined which will linearize curve 68, as represented by curve 72. From curve 72, the computer 52 can determine a basis weight value, w, for the measured values of $I_1...I_n$ detected over a given period of time, or over a set of locations, or the like.

It is a particular object of the present invention to provide a method and apparatus for "correcting" the slope of curve 72, to better take into account the nonlinear averaging that occurs due to nonuniform distribution of the mass making up the process sheet being measured. Schematically, the present invention adjusts the slope of curve 72, for example, to the slopes represented by curves 74, 76, 78, and 82, in order to more accurately determine the basis weight w at different levels of mass nonuniformity represented by $a_1$, $a_2$, $a_3$, and $a_4$ respectively.

In one particular implementation of the invention, the step of determining an index Z commensurate with the degree of nonuniformity of the variable, i.e. mass, is achieved by measuring that nonuniformity independently of the steps associated with the source head 28 and detector head 32 of the beta gauge. For example, as shown in FIG. 2, a separate gauge 58, 62, such as the type commonly referred to as a "formation" gauge, can be positioned at a known location relative to the beta gauge for measuring formation quality. On a paper machine the formation gauge would normally be mounted immediately adjacent to the beta gauge and in-line upstream or downstream with respect to the paper machine direction so that both sensors are measuring the same portion of the process as it passes through the sensors. Conventionally, such formation gauge is used as a quality assurance tool to inspect the paper prior to further processing or delivery. In the present invention, the formation gauge is coupled through interface 60 to the computer 52 of the measurement and control system. The output from the formation gauge 58, 62 is thus used to correct the basis weight determined conventionally by the beta gauge, by an index commensurate with the degree of process material nonuniformity.

One suitable formation gauge is available under the Optipak trademark from Process Automation Business, Inc., a subsidiary of Combustion Engineering, Inc. This gauge is based on principles described in U.S. Pat. Nos. 3,435,240, Radiation Sensitive Structure Determining Apparatus, Donald C. Brunton; 3,435,241, Structure Inspection Equipment, W. P. Hickey et al; and 3,435,242, Formation Inspecting Arrangement, R. W. Kinne, the disclosures of which are hereby incorporated by reference. The formation gauges described therein, and others that are available in the industry, typically rely on optical transmission characteristics, i.e., the visible light wavelengths portion of the electromagnetic spectrum.

Figure 5:
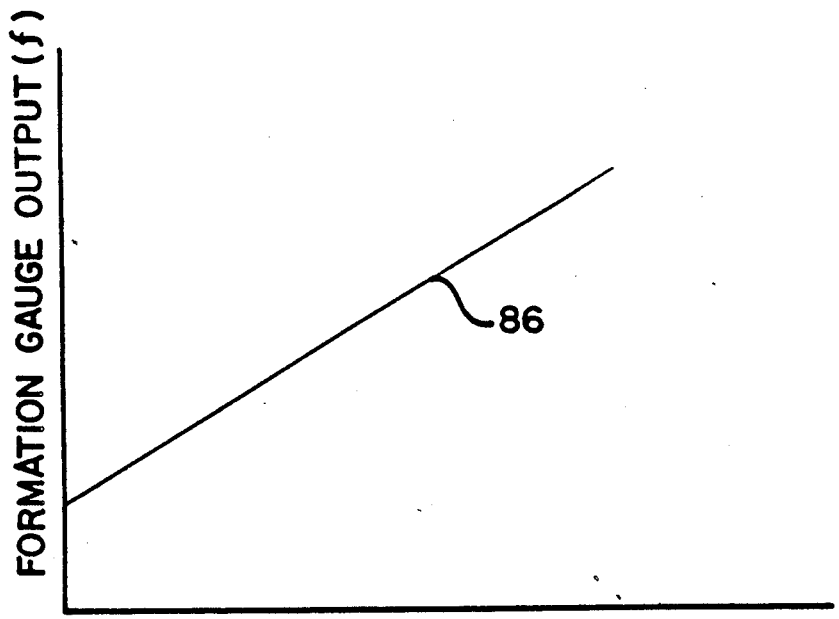
FIG. 5 is a graphic representation of the determination of a slope correction index using a formation gauge output to correct the slope associated with uniform sheet material as described with reference to FIG. 4.

The formation gauge is calibrated with the basis weight gauge, using the same set of standard laboratory samples or alternately, using samples from the actual paper machine where the sensors are to be deployed. As illustrated in FIG. 4, a single linear calibration curve 72 is developed for the beta gauge using calibration samples which represent homogeneous process material. Next, samples of known average basis weight comprised of nonhomogeneous process material are read on both the basis weight gauge and the formation gauge. The basis weight measurement errors for the nonhomogeneous samples are correlated with the formation gauge output values (f-values). A best fit curve, such as 86 shown in FIG. 5, is established and stored in the computer. This relates the formation gauge output (f) to a first type of index $Z = A' + B'f$. This particular index will herein be referred to as the formation gauge quality index $Z(f)$.

$Z(f)$ is in effect a slope correction index, which can best be understood with reference to FIG. 4. Since the beta gauge is calibrated for homogeneous samples which have no nonlinear averaging, it will always interpret a radiation transmittance reading by converting it to a basis weight value using curve 72. The formation gauge has been calibrated (FIG. 5) to provide the percent error, or percent shift in the true calibration curve for nonhomogeneous materials. The dashed curves 74, 76, 78, and 82 therefore represent the true beta gauge response curves responding to formation gauge correction-values of $a_1$, $a_2$, $a_3$, and $a_4$ respectively. For example, if the formation gauge indicates formation nonuniformity of $a_3$, then the slope correction index $Z(f)$ has a value indicated by lead line 84. The corrected basis weight w, can thus be expressed as $$w' = w(1+Z) = w(1+(A'+B'f)) \tag{5}$$

Figure 6:
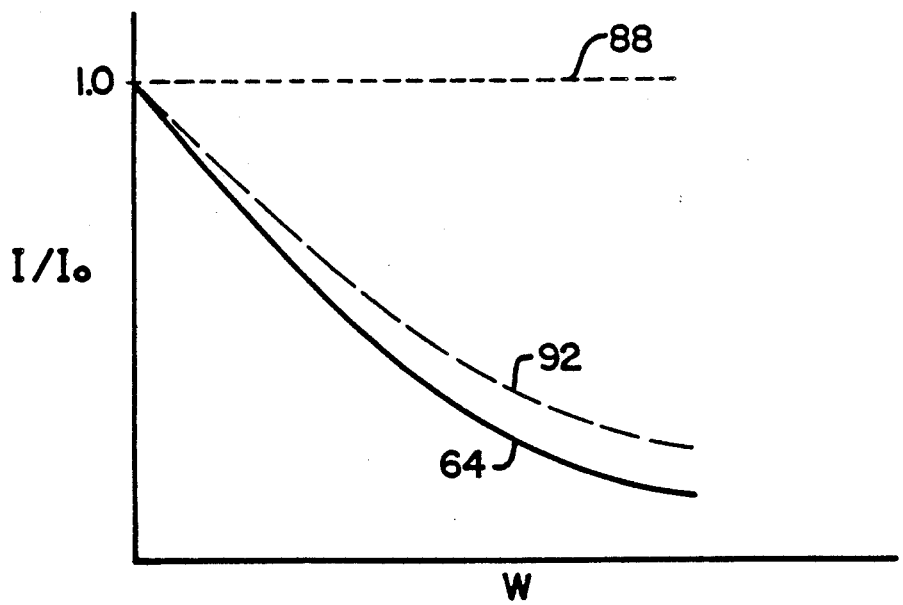
FIG. 6 is a graphic representation of the effect of material voids, which represent the limit in reduced basis weight areas, on the relationship between the radiation beam transmittance and basis weight.

FIG. 6 illustrates conceptually how the relationship between transmittance and basis weight might be corrected empirically for the situation of nonhomogeneous process material. In FIG. 6, curve 64 is identical to curve 64 of FIG. 3, representing the relationship of equation (1). Curve 88 shows this same relationship for the hypothetical case where the sheet material is composed entirely of voids, i.e. there is no radiation attenuation. If the sheet material were to actually consist of 90% homogeneous solids and 10% voids, the relationship between transmittance and basis weight would be depicted by curve 92 which is a composite made up of 90% of curve 64 and 10% of curve 88. In this invention, the composite curve 92 for nonhomogeneous solids is obtained from the slope correction index $Z(f)$, as applied to version 72 of curve 64, as shown in FIG. 4.

In a different embodiment of the present invention, the step of determining the index Z is based on a statistical representation of the transmittances or their equivalent measured parameter, and utilizes such a statistical index $Z(s)$ to obtain a corrected, or compensated, basis weight.

Again, in the context of measuring the basis weight of a paper sheet, for this embodiment the relationship (3) is used to define the measured process basis weight as follows:

$$w = -K \ln(X)/(u_o + u_1\ln(X) + u_2\ln^2(X) + u_3\ln^3(X)) \tag{6}$$

where K is a stored constant for expressing basis weight in units of grams per square meter or other appropriate units, X is the parameter $I_{avg}/I_o$, and $I_{avg}$ equals the average value of the measured radiation intensities $I_1$, $I_2$, ..., $I_n$. The plurality of intensities $I_1...I_n$ can be obtained with a stationary sensor which samples the process material periodically as it passes through the heads, or alternately, the gauge can move relative to the process material and obtain a multiplicity of measurements that vary over space and time. In another possible implementation, a plurality of gauges can be spaced apart and measure intensities simultaneously or in sequence.

The statistical approach begins from the premise that a quantitative relationship exists between the variance of the process basis weight w and the variance of the measured radiation intensity I, in the basis weight gauge arrangement 28, 32 shown in FIG. 2. The existence of a relationship is apparent from equation (1). One form for expressing this relationship is through the process resolution expression derived from equation (1), $$\% \text{ process}/\% \text{ radiation} = \frac{(d(w)/w)*100}{d/(I/I_o)} = \frac{e^{uw}*100}{uw} \tag{7}$$

Figure 7:
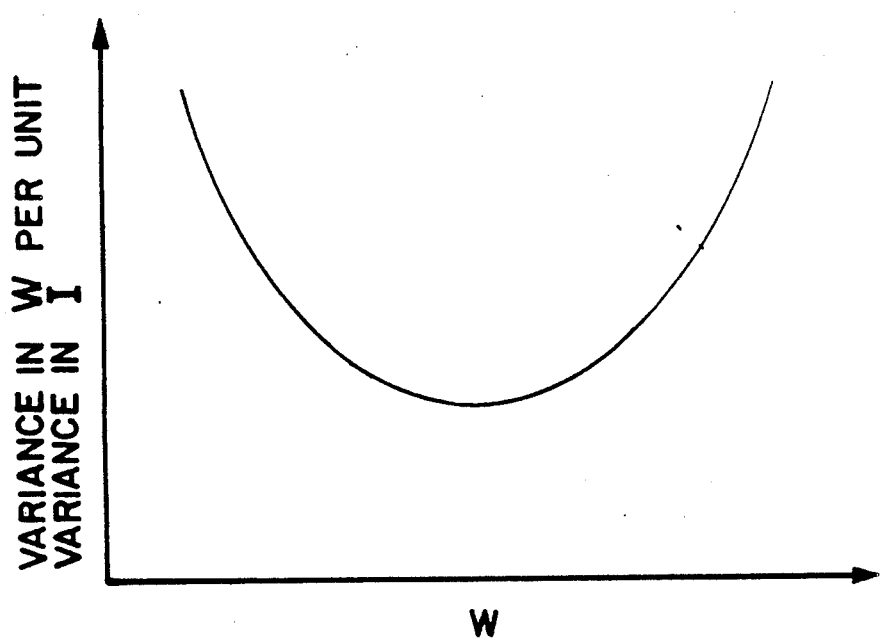
FIG. 7 is a graphic representation of the process resolution expression of Equation (7) which illustrates the relationship between a change in basis weight and the corresponding change in the measure radiation beam intensity as a function of basis weight for a basis weight gauge.

The general form of this relationship is shown in FIG. 7 and w is of the form given in equation (6).

In the expression shown in equation (7), the function $$s = (d(w)/w)*100 \tag{8}$$

can be defined. For paper measurements with a beta gauge, it has been shown that there is a high correlation between the measured basis w and the true weight w' when using the function s in the following expression:

$$w' = w\left(1 + \frac{(A + B(s^2 w))}{100}\right) \quad (9)$$

where A and B are the intercept and slope values from a linear fit of data obtained by measuring basis weight for a number of samples of varying nonuniformity of mass distribution. It has been found that a particularly good correlation for one model of basis weight sensor utilizes the values A=1.34 and B=31.9, when s is a decimal value.

The form of equation (9) is obtained from the following mathematical derivation:

1. Let w represent an instantaneous measured value of basis weight for a portion of the process material corresponding to measurement area 42. And, let w, equal the true average basis weight for that measurement area. Then equation (1) can be written in the form $$I = I_o e^{-uw'} e^{-u(w-w')} \quad (10)$$

where the second term, $e^{-u(w-w')}$, is, in effect, the error term. Expand the error term in a Taylor series about the true average weight w', and assume that uw' is approximately equal to 1 and the root mean square value of $((w-w')/w')$ is approximately 0.25. These assumptions are reasonable under typically optimal operating conditions.

2. Express the average measured signal $I_{avg}$ as w varies within the measurement, either due to spatial averaging within the radiation beam or time averaging of several locations on the sheet, or both, by $$I_{avg} = I_o e^{-uw'}\left[1 - 0 + \frac{(uw')^2}{2!} W^2 - \frac{(uw')^3}{3!} W^3 + \ldots\right] \quad (11)$$

where $W^2$=the average value of $((w-w')/w')^2$, etc.

3. If w' is the true basis weight average of the measurement set, then the first order term is zero and if the distribution of w about w' is Gaussian, $W^3 = 0$. From step 2 above, $W^4$ is negligible. Thus, $$I_{avg} \approx I_o e^{-uw'}\left[1 + \frac{(uw')^2}{2!} W^2\right] \quad (12)$$

4. Let $w'' = -(1/u)\ln(I_{avg}/I_o)$, which represents the measured average value of w based on $I_{avg}$ and the attenuation coefficient u determined for a perfectly uniform sheet of the same material as the process material. By using the results of step 3 and the identity $$\ln(1 + x) = x - \frac{x^2}{2} + \frac{x^3}{3} - \frac{x^4}{4} + \ldots$$

where $-1 < x < +1$, $$\frac{w'' - w'}{w'} = \frac{-uw'}{2} W^2$$

This implies that a gauge so calibrated will always read low by the quantity on the righthand side of the previous equation.

5. A slope correction factor $$\frac{w'}{w''}$$

can then be derived from $$\frac{w''}{w'} = 1 - \frac{uw'}{2} W^2 \quad (13)$$

and the true average basis weight can be expressed as $$w' = w''(1 + (A + BW^2)) = w''\left(1 + \frac{uw'(w-w')^2}{2(w')^2}\right) \quad (14)$$

6. Thus, the statistical function s can be defined to satisfy $w' = w''$ $$\frac{(1 + (A + Bs^2 w))}{100}.$$

S can be approximated by the fractional standard deviation of the instantaneous measured average value of w relative to the mean measured average value of w'', and thus a "beta gauge function" s can be substantially continually computed on-line and used to compute w' on-line.

Similarly, with respect to the first embodiment described above, the index Z(f) is an empirical counterpart for the index Z(s), i.e., if we let $w' = w(1+Z)$, i.e., $Z = (w'-w)/w$, then $Z(f) = A' + B'^* f$ and $Z(s) = A + Bs^2 w$.

Table 1 summarizes data by which the measured basis weight for seven paper samples was corrected to take into account the property of formation in paper, using early embodiments of the two techniques described above. The formation gauge output f was determined by the Optipak formation gauge mentioned above. The basis weight w and standard deviation s were measured with a TLP1 model beta gauge which uses the radioisotope Pm-147 as a source. The paper samples covered a wide range of formation values. Low formation values represent "good" quality products while high values indicate poorer quality products.

TABLE

| Sample # | True Basis Wt (w') | Formation Gauge Value (f) | Beta Gauge Statistical Value (s) |
|---|---|---|---|
| 1 | 59.98 | 29.4 | 3.96 |
| 2 | 77.45 | 11.0 | 2.00 |
| 3 | 73.88 | 10.4 | 1.72 |
| 4 | 89.00 | 11.5 | 2.29 |
| 5 | 46.16 | 15.5 | 2.52 |
| 6 | 79.02 | 10.2 | 2.12 |
| 7 | 90.51 | 45.6 | 4.68 |

$w'(f) = w(1 + A' + B'f)) = w(1 + (-3.6 \times 10^{-4} + 2.1 \times 10^{-3} f))$ with correlation at 0.93, and $$w'(s) = w\left(1 + \frac{(1.34 + 31.9\, s^2 w)}{100}\right), \text{ with correlation at 0.98}$$

For equations (5) and (9), the slope and intercept values for A', B', A, and B can be determined from the data in Table 1. For these early embodiments, the corrected basis weight values w'(f) and w'(s) for the seven measured samples are then illustrated in Table 2.

TABLE 2

| Sample # | True Basis Wt (w') | Initial Beta Gauge Reading (w) | Corrected Beta Gauge Value w' (f) | Corrected Beta Gauge Value w' (s) |
|---|---|---|---|---|
| 1 | 59.98 | 55.72 | 59.14 | 58.14 |
| 2 | 77.45 | 75.48 | 77.20 | 77.24 |
| 3 | 73.88 | 72.39 | 73.94 | 73.87 |
| 4 | 89.00 | 86.7 | 88.76 | 89.15 |
| 5 | 46.16 | 45.14 | 46.59 | 46.17 |
| 6 | 79.02 | 77.13 | 78.75 | 79.04 |
| 7 | 90.51 | 84.05 | 92.07 | 90.49 |

The computation of the corrected basis weight w' as a function of the value f, obtained from the formation gauge data, resulted in a positive correlation of 0.93 in the test illustrated by Table 1. The correlation using the statistical function s from the standard deviation in the beta gauge measurements resulted in a positive correlation of 0.98. These examples illustrate the effectiveness of this invention for compensating measurement sensors that have a nonlinear response with respect to the process variables being measured when that process exhibits a nonhomogeneous distribution of the measured variable within the measurement area of the sensor.

It should be appreciated that other techniques are also available for implementing applicant's invention. For example, an analytical technique can be employed based on the effect on the mass attentuation coefficient u, of a measurable variable that is not normally included within the mathematical expression for u. The mass attenuation coefficient u in the transmission gauge radiation attenuation equation (3) can be thought of as a probability number. It is the probability that energy will be lost as the radiation goes through the sheet to be measured. This probability changes with changes in the formation of the sheet due to the nonlinear averaging effect. By correlating u with the formation value f, the formation gauge can be calibrated to read out directly in terms of u or d(u), i.e., differential u. In the original calibration of the beta gauge, u can be determined as a function of $I/I_o$ for the homogeneous sheet material (e.g., using equation 3). Then, with the radiation attentuation equation in the form, $$I/I_o = e^{-(u+d(u))pt}, \text{ or}$$

$$pt = \ln(u+d(u))$$

basis weight (pt) can be found analytically from the beta gauge and formation gauge measurement values.

In essence, the analytical technique is a method for operating an instrument to determine the average value of a process parameter (pt) which is continually changing within the target region of the instrument, where the instrument includes a sensor arrangement responsive to changes in the parameter. The parameter is dependent on a plurality of detectable variables, for example, a first variable ($I/I_o$) and a second variable (formation) each of which produces a respective non-linear response in the sensor arrangement when the parameter changes linearly. The attenuation coefficient (u) is preferably expressed mathematically, for example, as set forth in equation (3), such that the parameter (pt) can be mathematically approximated as a linear relationship on the first variable ($I/I_o$) if the target region is homogeneous with respect to the second variable, e.g., per equation (2). The method further includes the step of generating an adjustment signal index commensurate with the deviation from homogeneity of the second variable as measured in the region, for example, from the formation gauge. The instrument has associated therewith a stored quantitative relationship of the effect of a change in the second variable on the coefficient (u), so that a control signal can be generated from the instrument, representing the average value of the parameter in the region. This average value is dependent on the average value of the first variable ($I/I_o$) in the region, the mathematical coefficient (u), and the adjustment signal as measured in the region and as accounted for through the stored quantitative relationship. In effect, the analytical technique embodiment of the invention uses an analytical index Z(f) based on the differential of the coefficient (u) with respect to, for example, the formation variable.

We claim:

1. A method for controlling an industrial process by measuring the average intensity of radiant energy emanating from a process material, the material having a non-uniform distribution of a particular variable in a given portion of the material, the variable interacting with incident radiant energy from a source to nonlinearly influence the measured emanating intensity attributable to said given portion, wherein the method comprises:

directing a source of radiant energy having a reference intensity Io into one portion of the process material such that the source radiation interacts with the material and produces a radiant energy pattern that emanates from the material at an instantaneous intensity I;

positioning a sensor to detect the instantaneous intensity I of radiant energy emanating from the process material;

determining an index Z commensurate with the degree of nonuniformity of the variable in said portion of the material; and generating a process control signal from a quantitative relationship among I, Io, and said index Z.

2. The method of claim 1, wherein the step of determining an index Z includes the step of measuring the nonuniformity of the variable independently of the steps of detecting the intensity I.

3. The method of claim 1, wherein the step of determining an index Z includes the steps of,
 (a) acquiring a plurality of measurements of I,
 (b) determining the average intensity $I_{avg}$ of the plurality of measurements, and
 (c) determining a statistical relationship between the instantaneous intensities I and the average intensity $I_{avg}$.

4. The method of claim 2, wherein said variable is the mass of the material and the step of determining an index Z includes measuring the degree of nonuniformity in the mass distribution of the material.

5. The method of claim 4, wherein the material is in sheet form and the step of measuring the degree of nonuniformity of mass distribution includes generating an output signal from a formation gauge.

6. The method of claim 3 wherein the step of determining a statistical relationship includes computing the standard deviation of a signal commensurate with the measurements of I over a predetermined statistical sampling set.

7. The method of claim 6, wherein the predetermined sampling set is a predetermined number of measurements of the process control signal during a predetermined period of time.

8. The method of claim 6, wherein said predetermined sampling set is a predetermined number of process control signals measured substantially simultaneously over a plurality of substantially similar sets of sources and detectors associated with the same process.

9. The method of claim 1, wherein the interaction of the source energy with said process material under conditions of uniform distribution of said variable is characterized by the relationship $I = I_o e^{-uw}$, where u is the effective interaction cross section per unit of process material mass and w is the instantaneous inferred process variable in terms of average mass of process material per unit area of material, and the step of generating a process control signal includes generating a process control signal w, from the relationship $w' = w(1+Z)$.

10. The method of claim 9, wherein the step of generating the process control signal w' includes computing the value of w from the relationship $$w = -K \ln(I/I_o)/u_o + u_1 \ln(I/I_o) + u_2 \ln^2(I/I_o) + u_3 \ln^3(I/I_o)).$$

11. The method of claim 9 wherein the step of generating a process control signal includes generating a signal of the form $$w' = w(1 + (A' + B'f))$$

where A', B' are constants and f is commensurate with a measurement of the degree of nonuniformity of said variable.

12. The method of claim 9 wherein the step of generating a process control signal includes generating a signal of the form $$w' = w\left(1 + \frac{(A + B(s^2 w))}{100}\right)$$

where A, B are constants and $s^2$ is the fractional standard deviation of the instantaneous measured average value of w relative to the mean measured average value of w.

13. A method of operating an instrument for determining the average value of a process parameter which is continually changing within the target region of a sensor associated with the instrument, the parameter being dependent on a plurality of variables, a first and a second of said variables producing respective nonlinear responses in the sensor when said variables change linearly, the method comprising the steps of:

establishing a mathematical coefficient which when combined with the sensor output for said first variable, approximates a linear relationship between the process parameter and the variable if the target region is homogeneous with respect to the second variable;

generating an adjustment index signal commensurate with the deviation from homogeneity of said second variable as measured in the region;

storing a quantitative relationship of the effect of a deviation in said second variable on the said coefficient;

generating an instrument output signal proportional to the average value of the process parameter, in which the average value of the parameter in the region is computed as dependent on the average value of the first variable in the region, the mathematical coefficient and said adjustment signal.

14. The method of claim 13, wherein the process parameter is a property of a paper sheet during production, and the step of generating an output signal includes generating a signal w' of the form $$w' = \ln(I/I_o)/(u + Z(f))$$

where w' = signal generated for controlling paper production process $I/I_o$ = the first variable, commensurate with a radiation attenuation property of the sheet as measured by the sensor u = the mathematical coefficient, and Z(f) = the quantitative relation between a change in the second variable f, and the coefficient.

15. The method of claim 14, wherein the step of generating an adjustment signal includes measuring the formation of the paper sheet.

16. An instrument for determining the average value of a process parameter in a region of the process by measuring a first variable that is nonlinearly dependent on a changing property of the process, comprising:

a first sensor for measuring the average value of the first variable in a region of the process;

means for storing a mathematical coefficient representative of a homogeneous distribution of said property within the region;

means coupled to the first sensor for storing the coefficient, for combining the sensor measurement and the stored coefficient to generate a preliminary output signal indicative of the average value of the process parameter in the region as a function of said first variable;

means for generating an index commensurate with the degree of nonhomogeneity of said changing property in the region; and means coupled to the means for generating a preliminary output signal and the means for generating an index, for adjusting said preliminary output signal to generate a compensated average value of the process parameter in response to changes in the index.

17. The instrument of claim 16, wherein the first variable is an exponential function of the parameter, the coefficient is a function of the first variable, and the index is commensurate with a second variable.

18. The instrument of claim 17, including means for statistically monitoring the first variable, and wherein the second variable is derived from a statistical property of the first variable.

19. The instrument of claim 16, including a second sensor for measuring the nonhomogeneity of said property in said region, and wherein the means for generating an index is coupled to said second sensor.

20. The instrument of claim 16, wherein the instrument is connected to a paper sheet production process, and wherein, the first variable is commensurate with the radiation attenuation property of the sheet in the process;

the mathematical coefficient is a function of the first variable; and the index is commensurate with the nonhomogeneity of the mass distribution in the region.

* * * * *

UNITED STATES PATENT AND TRADEMARK OFFICE
CERTIFICATE OF CORRECTION

PATENT NO. : 4,990,784
DATED : February 5, 1991
INVENTOR(S) : John R. Dukes, Mason L. Thompson It is certified that error appears in the above-identified patent and that said Letters Patent is hereby corrected as shown below:

Col. 12, line 11 of Claim 1, "Io" should be --$I_o$-- .

Col. 12, line 23 of Claim 1, "Io" should be --$I_o$-- .

Col. 13, line 11 of Claim 9, "w" should be --w'-- .

Col. 13, lines 4-6 of Claim 10, the equation should be on same line.

Col. 14, line 10 of Claim 16, after "sensor" insert --and the means-- .

Signed and Sealed this

Fifteenth Day of December, 1992

Attest:

DOUGLAS B. COMER

*Attesting Officer*   *Acting Commissioner of Patents and Trademarks*